United States Patent [19]

Matsuki et al.

[11] Patent Number: 5,268,287
[45] Date of Patent: Dec. 7, 1993

[54] PHOSPHAZENE POLYMER FOR IMMOBILIZING BIOLOGICALLY ACTIVE SUBSTANCES

[75] Inventors: Toshitsugu Matsuki; Noritsugu Saiki, both of Matsuyama; Shingo Emi, Daito, all of Japan

[73] Assignee: Teijin Limited, Osaka, Japan

[21] Appl. No.: 603,500

[22] Filed: Oct. 26, 1990

[30] Foreign Application Priority Data

| Oct. 27, 1989 | [JP] | Japan | 1-278363 |
| Nov. 22, 1989 | [JP] | Japan | 1-301903 |
| Nov. 24, 1989 | [JP] | Japan | 1-303195 |
| Nov. 27, 1989 | [JP] | Japan | 1-304797 |
| Apr. 2, 1990 | [JP] | Japan | 2-85012 |

[51] Int. Cl.$^5$ .................. C12N 11/06; G01N 33/549; C08G 79/02; C07K 17/00
[52] U.S. Cl. ............... 435/181; 435/180; 435/803; 435/815; 436/531; 436/532; 528/399; 530/413; 530/815; 530/816
[58] Field of Search ............... 435/177, 180, 181, 803, 435/815; 436/531, 532; 530/815, 413, 816; 528/399

[56] References Cited

U.S. PATENT DOCUMENTS

| 3,666,733 | 5/1972 | Epton | 435/180 X |
| 3,669,841 | 6/1972 | Miller | 435/177 X |
| 4,451,619 | 5/1984 | Heilmann et al. | 525/379 |

OTHER PUBLICATIONS

Guiseppi-Elie, et al., Journal of Polymer Science, vol. 23, 1985, pp. 2601-2613.
Allcock et al., Macromolecules, vol. 16, No. 9, 1402-1406, 1983.
World Patents Index Latest, Derwent Publications, Ltd., London, GB; AN 85-163620 & SU-A-1 085 993 (Moscow Mendeleev) Apr. 15, 1984.
Macromolecules, vol. 19, No. 6, Jun. 119, 1986, pp. 1502-1508; H. R. Allcock: "Covalent Linkage of Proteins".

*Primary Examiner*—David M. Naff
*Attorney, Agent, or Firm*—Sughrue, Mion, Zinn, Macpeak & Seas

[57] ABSTRACT

A phosphazene polymer for immobilizing biologically active substances such as enzymes is prepared that does not lower activity originally possessed by the biologically active substance and does not contain a functionality which can adsorb undesired substances. The polymer has organic radicals having a functional group capable of binding a biologically active substance and organic radicals which are non-reactive and hydrophilic. The non-reactive and hydrophilic organic radicals are preferably prepared by reacting a side chain of the polymer having a primary amino group with formaldehyde or by diazotizing the primary amino group followed by hydrolysis to form a hydroxyl group. A biologically active substance immobilized on the polymer can be used to separate a substance that has affinity for the immobilized biologically active substance.

7 Claims, No Drawings

PHOSPHAZENE POLYMER FOR IMMOBILIZING BIOLOGICALLY ACTIVE SUBSTANCES

BACKGROUND OF THE INVENTION

1. Field of the Invention

The present invention relates to a biologically active substance-immobilized carrier comprising phosphazene polymer, a carrier comprising phosphazene polymer for immobilizing a biologically active substance, process as for a production thereof, and to the use thereof.

2. Description of the Related Art

Although biologically active substances such as antibodies, enzymes and the like are usually present in a form of solution, if they are immobilized on a solid carrier, their usefulness is largely expanded. The nature of the solid carrier, however, has various limitations, depending on the use of the carrier. For example, where the solid carrier is used for an affinity chromatography, the solid carrier must not adsorb substances other than a desired substance, i.e., a non-specific adsorption will not occur. Accordingly, to use of a synthetic polymer as a carrier for an affinity chromatography is not always successful, and currently, modified carbohydrate materials derived from naturally occurring carbohydrates such as agarose, cellulose and the like are mainly used.

Nevertheless, since synthetic polymer carriers are advantageous in comparison with modified carbohydrate carriers, in that they can be easily shaped, are resistant to on infection of microorganisms such as fungi, to a high pressure, and a high flow rate, many attempts have been made to use carbohydrate materials as an affinity chromatography carrier and some are actually used. It should be noted, however, that synthetic polymer carriers are disadvantageous in that an activity of a biologically active substance immobilized on a synthetic polymer carrier is lower than that of a biologically active substance immobilized on a carbohydrate carrier.

Japanese Unexamined Patent Publication (Kokai) No. 1-30650 describes a carrier comprising phosphazene polymer for immobilizing a biologically active substance wherein functional groups capable of immobilizing a biologically active substance (ligand) (or groups which can be converted to functional groups capable of immobilizing a biologically active substance) have been introduced in a surface lower portion of the carrier. The functional groups are introduced by treating a shaped polyphosphazene article.

Macromolecules 19 (6) 1505, (1986) describes an immobilization of an enzyme using a carrier wherein polybisaryloxyphosphazene is carried in porous alumina and amino groups are introduced in the phosphazene polymer present in a surface lower portion of the carrier.

When using the above-mentioned carriers in affinity chromatography or diagnostics, however, if side chains not having a functional group capable of bringing a ligand are hydrophobic, substances other than those having an affinity to the ligand are adsorbed to the carrier via the hydrophobic side chains, resulting in a lowering of the separation efficiency and diagnostic accuracy.

In the carrier described in the Japanese Unexamined Patent Publication (Kokai) No. 1-30650, since many functional groups capable of binding a biologically active substance exist, a large amount of the biologically active substance can be quantitatively immobilized, but sometimes a third dimensional structure of a biologically active substance is changed and an active site of the biologically active substance is inactivated by the functional groups. Moreover, functional groups which are not bonded to the biologically active substance could bind to biologically active substances other than that which should be a ligand, and if such solid carriers are used in affinity chromatography, a desired substance may be contaminated with substances not having an affinity to the ligand.

SUMMARY OF THE INVENTION

Accordingly, the present invention provides a biologically active substance-immobilized carrier which contains an abundant biologically active substrate immobilized thereon, does not lower a biological activity originally possessed by the biologically active substance, and does not contain an undesired functionality which would adsorb undesired substances.

More specifically, the present invention provides a biologically active substance-immobilized carrier comprising phosphzene polymer having side chains, characterized in that, among side chains of the phosphazene polymer present in at least the surface layer portion of the carrier, the biologically active substance has been immobilized to at least a portion at the side chains and a remaining portion of the side chains substantially consists of organic radicals which are non-reactive and hydrophilic.

Moreover, the present invention provides a carrier immobilizing a biologically active substance, which carrier comprises a phosphazene polymer having side chains, characterized in that side chains of the phosphazene polymer present in at least a surface layer portion of the carrier substantially consist of organic radicals having a functional group capable of bringing the biologically active substance and organic radicals which are non-reactive and hydrophilic.

The present invention also provides a process for a production of a carrier for immobilizing a biologically active substance, characterized by reacting a shaped polyphosphazene article with a solution containing a bifunctional aldehyde and formaldehyde, wherein at least a surface layer portion of the article is composed of a phosphazene polymer which has side chains having a primary amino group.

The present invention further provides a process for a production of a carrier for immobilizing a biologically active substance, by reacting a shaped polyphosphazene article with a bifunctional aldehyde compound, wherein at least a surface layer portion of the article is composed of a phosphazene polymer which has side chains having a primary amino group, and then diazotizing remaining primary amino groups followed by hydrolysis to form hydroxyl groups, characterized by reacting the bifunctional aldehyde compound at a pH of between 1.5 and 5.

The present invention still further provides a process for a production of a carrier for immobilizing a biologically active substance, by treating a shaped phosphazene article with a bifunctional aldehyde compound at a pH of between 1.5 and 5, wherein at least a surface layer portion of the article is composed of a phosphazene polymer which has side chains having a primary amino group, diazotizing remaining primary amino groups, and hydrolizing resulting diazonium salt groups to hydroxyl groups, characterized by blocking aldehyde groups with a protecting agent and reducing imino bonds formed by the treatment with the bifunctional aldehyde compound, prior to the diazotizing reaction, and removing the protecting groups after the diazotizing reaction.

The present invention also provides a process for production of a carrier for immobilizing a biologically active substance, by converting a shaped polyphosphazene article wherein at least a surface layer portion of which has side chains having a primary amino group, to the carrier wherein at least a portion of the amino groups have bonded to bifunctional aldehyde and remaining side chains having a amino group have been converted to side chains substantially consisting of organic radicals which are non-reactive and hydrophilic, characterized by crosslinking the article prior to binding a portion of the amino groups to the bifunctional aldehyde, to introduce functional groups capable of binding a biologically active substance.

Moreover, the present invention provides a process for a production of a biologically active substance-immobilized carrier, characterized by reacting a biologically active substance with a carrier comprising a phosphazene polymer having side chains, wherein side chains of the phosphazene polymer present in at least a surface layer portion of the carrier substantially consist of organic radicals having a functional group capable of binding the biologically active substance and of organic radicals which are non-reactive and hydrophilic.

The present invention also provides a process for production of a biologically active substance-immobilized carrier, characterized by reacting a biologically active substance with a carrier comprising a phosphazene polymer having side chains, wherein side chains of the phosphazene polymer present in at least a surface layer portion of the carrier substantially consist of organic radicals having a functional group capable of binding the biologically active substance, and then converting side chains having the functional group which has not reacted with the biologically active substance to side chains which are non-reactive and hydrophilic.

The present invention still further provides a process for separating a desired substance from a mixture containing the desired substance, characterized by using a carrier wherein a biologically active substance having a specific affinity to the desired substance has been immobilized to the carrier.

DESCRIPTION OF THE PREFERRED EMBODIMENTS

The present invention is based on the following inventive activities:

(1) It was found that, where a biologically active substance is immobilized to a portion of side chains of a polymer having a polyphosphazene backbone, and a remaining portion of chains is made organic radicals which are non-reactive and hydrophilic, a resulting modified phosphazene polymer does not provide a non-specific adsorption and does not lower the activities of the immobilized biologically active substance;

(2) An immobilizing carrier useful for the preparation of the above-mentioned biologically active substance-immobilized carrier, and a process for the production thereof were found;

(3) It was found that the above-mentioned carrier for immobilizing a biologically active substance can be produced by reacting a phosphzene polymer which has side chains having an amino group with a dialdehyde compound (bifunctional aldehyde compound) to react only one of the aldehyde groups with the amino group of the side chain, according to various processes;

(4) A method was found of converting an amino group, which has not been reacted with the dialdehyde compound, to an organic group which is non-reactive and hydrophilic;

(5) A easy-handling process was found for the production of the above-mentioned carrier; and (6) A process was found for the production of the above-mentioned carrier in a fibrous form.

According to the present invention, there is provided a biologically active substance-immobilized carrier comprising a phosphazene polymer having side chains, characterized in that, among side chains of the phosphazene polymer present in at least a surface layer portion of the carrier, the biologically active substance has been immobilized to at least a portion of the side chains and a remaining portion of the side chains substantially consist of organic radicals which are non-reactive and hydrophilic.

The term "biologically active substance" as used herein means a substance which exhibits a specific interaction with a substance present in an organism, for example, a high molecular weight compound such as an enzyme, antibody, nucleic acid or the like, or a low molecular weight compound such as co-enzyme, hapten or the like, which is chosen according to the intended use of the carrier.

Phosphazene polymer is a polymer having a backbone composed of only phosphorus atoms and nitrogen atoms, and it is known that, since various moieties can be introduced to side chains of phosphazene polymer, the polymer can exhibit various properties.

The biologically active substance-immobilized carrier of the present invention composed of such a phosphazene polymer present in at least a surface layer portion of the carrier has side chains to which a biologically active substance has been immobilized, and remaining side chains substantially consist of organic radicals which are non-reactive and hydrophilic.

The phrase "Side chain to which a biologically active substance has been immobilized" as used herein means an organic radical to which a biologically active substance has been covalently bonded through an imine bond, an ester bond, an amide bond, an amino bond, an ether bond, a thioether bond or the like. One or more than one biologically active substance molecule can be immobilized to one side chain, and one biologically active substance molecule may be immobilized through one or more than one site. The biologically active substance may be immobilized either at a terminal region or at a central region of a side chain. Generally, from the view point of the resolution when used and an improvement of biological activities of an immobilized substance, a biologically active substance is preferably immobilized at one site on a terminal portion of a side chain.

A side chain preferably has up to 14 atoms, excluding atoms in branched chain and hydrogen atoms, and further, also excluding atoms in a biologically active substance. Moreover, a side chain is preferable wherein the number of continuous carbon atoms, to which a hetero atom such as an oxygen atom, nitrogen atom, sulfur atom, etc., is not directly bonded, is 5 or less. Where the number of chain atoms in more than 14, a reactivity for immobilizing a biologically active substance usually becomes lower. On the other hand where the number of continual chain atoms described above is more than 5, the non-specific adsorption may be increased, or the activity of an immobilized substance may be lowered. Note, although a side chain can have branched chains, the number of atoms forming such a branched chain is preferably smaller than the number of atoms forming a side chain, calculated as above. (Note the number of hydrogen atoms is not included.)

According to the present invention, among side chains present in at least a surface layer portion of the carrier, side chains other than those to which a biologically active substance has been immobilized consist substantially of organic radicals which are non-reactive and hydrophilic. In this case, the term "consist substantially of" means that it is not necessary that all of the remaining side chains are the above-mentioned organic radicals, and other organic radicals can be present to an extent such that the non-specific adsorption is reduced and an activity of the biologidally active substance is maintained. The amount of other organic radicals varies, depending on the intended purpose of use of the carrier but is usually up to 5% by mole, preferably up to 2% by mole.

In the present invention where in the carrier is used to separate and purify a biological component, the term "non-reactive organic radical" means an organic radical which does not react with biological components to form a covalent bond or, ionic bond etc. under a usual condition. On the other hand, "hydrophilic" organic radical means an organic radical which does not adsorb biological components by a hydrophobic interaction.

The non-reactive and hydrophilic organic radical is preferably an organic radical having an alcoholic hydroxyl group (designated "hydroxyl group" hereinafter) and/or an ethyleneoxy unit.

Where a side chain is an organic radical having a hydroxyl group, the hydroxyl group can be positioned on any side of the side chain, and one or more than one hydroxyl group can be present. Note, the number of atoms in a side chain counted from an atom bonded to the backbone to an atom which is most distant from the backbone (the longest chain length) is preferably up to 25, more preferably up to 20. A side chain can have as a branched chain an organic chain having fewer atoms than the number of the longest chain length (again excluding the number of hydrogen atoms). Where in a side chain at least 4 carbon atoms which do not bond to a hetero atom such as oxygen atom, nitrogen atom, sulfur atom or the like continue, there is a tendency for the hydrophilic property of the present invention to be reduced, resulting in a non-specific adsorption. Where the chain length of a side chain exceeds 25, the water solubility of phosphazene polymer is very high, and therefore, the phosphazene polymers should be crosslinked, for example, by a reaction therebetween, to lower this water solubility. On the other hand, where an extent of the crosslinage is too high, the transfer of a biologically active substance inside a carrier is suppressed, and thus a biologically active substance-immobilized carrier of the present invention cannot be efficiently produced; or when the biologically active substance-immobilized carrier is used, the transfer of biological component to a side to which the biologically active substance has been immobilized is suppressed, resulting in adverse effects such as a lowering of the activity of the biological component; or when the carrier is used for an affinity chromatography, the movement of biological components inside the carrier is delayed.

Where the non-reactive and hydrophilic side chain is an organic radical having ethylenoxy unit(s), an end of the ethylenoxy unit is preferably an aliphatic radical having 1 to 4 carbon atoms (which radical can contain hetero atom(s)) or a hydrogen atom (in this case the ethyleneoxide unit has a hydroxyl group). If the aliphatic group contains more than 4 carbon atoms, more than 3 carbon atoms to which the hetero atom is not 4 or more bonded must not continue.

Although the repeating number of ethyleneoxide units is not critical, if a side chain has too many ethyleneoxide units, the water solubility of the phosphazene polymer is too high, as in the case of hydroxyl groups described above, resulting in difficulties in the immobilization of a biologically active substance, or resulting in a lowering of an activity of a final product, and therefore, the number of ethyleneoxide repeating units preferably is chosen so that the highest chain length is no more than 25. The ethyleneoxide units may be sequentially present or may be interrupted.

The above-mentioned non-reactive, hydrophilic organic radical can contain an imine bond, amino bond, ester bond, amide bond, ether bond or other functional group, as long as the above-mentioned non-reactivity is satisfied.

In the present invention, a ratio of side chains to which a biologically active substance has been immobilized and side chains which are non-reactive and hydrophilic organic radicals, may be adequately chosen according to the use of the carrier. Since, generally, an immobilized biologically active substance is bulky, and further, a biological component which will interact with the immobilized substance is usually bulky, even if the number of the former increases the adsorption capacity, this does not increase in a dose dependent manner, and accordingly, the adsorption capacity may be lowered. Usually, the ratio of side chains to which a biologically active substance has been immobilized and side chains which are non-reactive and hydrophilic organic radicals, is preferably 1/1 to 1/100,000, more preferably 1/10 to 1/10,000.

The side chain (A) to which a biologically active substances (abbreviated as (L) hereinafter), and the non-reactive and hydrophilic side chains (B), are exemplified as follows. Note, the side chains in the formula are bonded to a phosphorus atom of a polyphosphazene backbone.

Side chain (A):

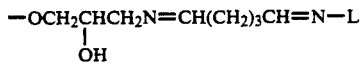

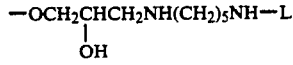

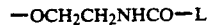

-continued

—OCH₂CHCH₂NHCO—L
　　　|
　　　OH

—(OCH₂CH₂)₂NHCO—L

—OCH₂CHCH₂O(CH₂)₄OCH₂CHCH₂O—L
　　　|　　　　　　　　　|
　　　OH　　　　　　　　　OH

—OCH₂CHCH₂S—L
　　　|
　　　OH

—NH(CH₂)₂NHCO—L

—NH(CH₂)₅CONH—L

—NH(CH₂)₅COO—L

—NH(CH₂)₆NHCOCH(CH₂)₂S—L
　　　　　　　　|
　　　　　　　　NH₂

—NH(CH₂)₂S—L

—NH(CH₂)₂COCH₂CH₂S—L

—NH(CH₂)₆NHCOCH₂NH—L

—NH(CH₂)₆NHCO(CH₂)₂CONH—L

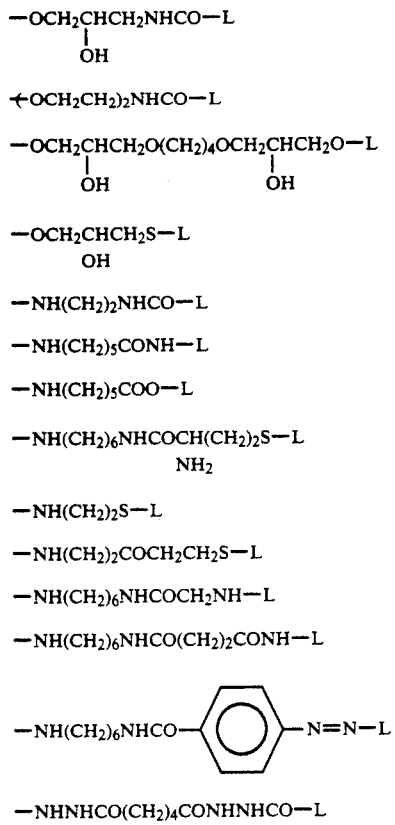

—NHNHCO(CH₂)₄CONHNHCO—L

Non-reactive hydrophilic side chain (B):

—OCH₂CH₂OH,

—OCH₂CH₂OCH₂CH₂OH

—OCH(CH₂OH)₂

—OCH₂CH(OH)CH₂OH

—OCH₂CH₂N=CH(CH₂)₃CH=NCH₂CH₂OH

—OCH₂CH₂NH(CH₂)₅NHCH₂CH₂OH

—OCH₂C-
　　H₂OCH₂CH₂N=CH(CH₂)₃CH=NCH₂CH₂OH

—OCH₂CH₂OCH₂CH₂NH(CH₂)₅NHCH₂CH₂OH

—OCH₂CH₂N=CH(CH₂)₃CH=NCH₂C-
　　H₂OCH₂CH₂OH

—OCH₂CH₂NH(CH₂)₅NHCH₂CH₂OCH₂CH₂OH

—OCH₂C-
　　H₂OCH₂CH₂N=CH(CH₂)₃CH=NCH₂C-
　　H₂OCH₂CH₂OH

—OCH₂CH₂OCH₂CH₂NH(CH₂)₅NHCH₂C-
　　H₂OCH₂CH₂OH

—OCH₂CH₂N=CH(CH₂)₃CH=NC(CH₂OH)₃

—OCH₂CH₂NH(CH₂)₅NHC(CH₂OH)₃

—OCH₂CH₂OCH₂CH₂N=CH(CH₂)₃CH=NC(C-
　　H₂OH)₃

—OCH₂CH₂OCH₂CH₂NH(CH₂)₅NHC(CH₂OH)₃

—OCH₂CH₂NHCH₂OH

—OCH₂CH₂OCH₂CH₂NHCH₂OH

—OCH₂CH₂OCH₂CH₂OCH₃

—OCH₂CH₂OCH₂CH₂OCH₂CH₂OCH₃

Preferable side chain (A):

—OCH₂CH₂N=CH(CH₂)₃CH=N— L

—OCH₂CH₂NH(CH₂)₅NH— L

—(OCH₂CH₂)₂N=CH(CH₂)₃CH=N—L

—(OCH₂CH₂)₂NH(CH₂)₅NH—L

Preferable side chain (B):

—OCH₂CH₂N=CH(CH₂)₃CH=NCH₂CH₂OH

—OCH₂CH₂NH(CH₂)₅NHCH₂CH₂OH

—OCH₂C-
　　H₂OCH₂CH₂N=CH(CH₂)₃CH=NCH₂CH₂OH

—OCH₂CH₂OCH₂CH₂NH(CH₂)₅NHCH₂CH₂OH

—OCH₂CH₂NHCH₂OH

—OCH₂CH₂OCH₂CH₂NHCH₂OH

—OCH₂CH₂OH

—OCH₂CH₂OCH₂CH₂OH.

Most preferable side chain (A):

—(OCH₂CH₂)₂N=CH(CH₂)₃CH=N—L

—(OCH₂CH₂)₂NH(CH₂)₅NH—L

Most preferable side chain (B):

—OCH₂C-
　　H₂OCH₂CH₂N=CH(CH₂)₃CH=NCH₂CH₂OH

—OCH₂CH₂OCH₂CH₂NH(CH₂)₅NHCH₂CH₂OH

—OCH₂CH₂OCH₂CH₂NHCH₂OH

—OCH₂CH₂OCH₂CH₂OH.

Next, the biologically active substance-immobilized carrier of the present invention is produced as follows.

Namely, a carrier for immobilizing a biologically active substance is placed in contact with a solution, usually an aqueous solution, containing a biologically active substance, to immobilize a desired amount of the biologically active substance. The carrier for immobilizing a biologically active substance includes two types of carriers. In the first type (designated carrier 1), side chains of a phosphazene polymer present in at least a surface layer portion of a shaped polyphosphazene article substantially consist of those side chains which have functional group(s) capable of immobilizing a biologically active substance. In the second type (designated carrier 2), side chains of a phosphazene polymer of the carrier consist of the above-mentioned reactive side chains, and non-reactive and hydrophilic side chains. To control an amount of an immobilized biologically active substance, a concentration of the substance in a reaction mixture, a reaction time, a reaction temperature, and a pH of the reaction mixture, etc., may be controlled. Alternatively, an amount of the functional group capable of immobilizing a biologically active substance may by previously by controlled.

Note, where an excess amount of the functional groups remains after the immoblization, the remaining functional groups should be converted to non-reactive and hydrophilic groups, because the remaining functional groups would lower the separation efficiency due to a non-specific adsorption thereof, and lower an activity of the immobilized biologically active substance. For the conversion, the reagent used may be suitably chosen depending of the kinds of functional groups to be inactivated. For example, where an amino group is to be inactivated, it can be hydroxy-methylated by formaldehyde, or reacted with an epoxy compound; carboxyl and aldehyde groups are preferably inactivated by the reaction to an alcohol using a reducing agent. The conditions for the above reaction are not critical, and are those under which an immobilized biologically active substance is not denaturated. Usually a temperature the same as or lower than a room temperature and a pH compatible with the immobilized biologically active substance are used.

Among the present processes, in an embodiment wherein the above-mentioned carrier 2 which has the minimum required amount of the side chains having functional group(s) capable of immobilizing a biologically active substance is used, it is not necessary to inactivate the excess amount of functional groups. Moreover, when a biologically active compound is immobilized, the possibility of a reaction of an active site of the substance with the functional group, resulting in a lowering of its activity, is low, and therefore, this embodiment is especially preferable. Although an optimum amount of the functional groups varies depending on the nature of the biologically active substance (especially its bulkiness) or the nature of a target substance which is to be interacted with the biologically active substance immobilized (especially its bulkiness), generally a ratio of the side chains having the functional group to the non-reactive and hydrophilic side chain is preferably 1/1 to 1/100,000, most preferably 1/10 to 1/10,000.

According to the present invention, the functional group capable of reacting with a biologically active substance to thereby immobilize the substance, includes not only those groups which by themselves can react with the biologically active substance, but also those groups which can be converted to groups capable of reacting with a biologically active substance. The groups are, for example, amino, carboxyl, thiol, aldehyde, epoxy, carboxyl and diazonium groups and the like, and among them, hydroxyl and carboxyl groups are usually activated with cyanogen bromide, carbodimide, N-hydroxysuccinimide or the like.

Where the functional group capable of immobilizing a biologically active substance is an aldehyde group, the aldehyde group reacts with an amino group of the biologically active substance to form an imino bond, resulting in an immobilization of the biologically active substance. In this case, since the imino bond is easily hydrolyzed, the imino bond is preferably reduced with a reducing agent such as sodium cyanoborohydride, borane-dimethylamine complex, boram-trimethylamine complex, tetramethylammonium borohydride, sodium borohydride or the like.

Where the functional group capable of immobilizing a biologically active substance is an amino group, the amino group is reacted with an aldehyde group in the biolgically active substance, reacted with a carboxyl group in the biologically active substrate in the presence of a dehydrating agent such as carbodiimide, or is reacted with a carboxyl group in the biologically active substance in which the carboxyl group has been previously converted to an active ester, so that the biologically active substance is immobilized to the carrier.

On the other hand, where the functional group capable of reacting with a biologically active group is a carboxyl group, the carboxyl group is reacted with an amino group in the biologically active substance after converting the carboxyl group to an active ester group or by using a dehydrating agent, so that the biologically active substance is immobilized to the carrier.

Next, the processes for production of the carrier 1 and carrier 2, used in the above-mentioned processes, are described. Note, the only differences between the carrier 1 and carrier 2 are the kinds of side chains and the ratio thereof present in a surface layer portion of the phasphazene polymer, and the processes for the production of the carriers 1 and 2 are substantially the same, and thus a process for the production of the carrier 2 is now described in detail.

The carrier can be produced by the following three processes.

(1) First, a phosphazene polymer having side chains which consist substantially of side chains (A') having functional group(s) capable of reacting with a biologically active substance, and side chains (B') which are non-reactive and hydrophilic, is prepared, and then the thus prepared phosphazene polymer is shaped, or the phosphzene polymer is coated on the surface of a shaped phosphazene polymer article having hydrophobic side chains, preferably consisting substantially of a trifluoroethoxy group.

(2) First, a phosphazene polymer having side chains which are different from the above-mentioned side chains (A') and (B') is prepared and shaped to a desired shape, and then the side chains of the phosphazene polymer present at least in a surface layer portion of the shaped article are converted to the side chains (A') having the functional group(s) capable of reacting with a biologically active substance and/or the non-reactive and hydrophilic side chains (B').

(3) In the above-mentioned processes (1) or (2), an excess amount of the side chains (A') having the functional group(s) capable of reacting with a biologically active substance is introduced in the phosphazene polymer (note, the side chains (B') have not to been contained, and in this case, the resulting carrier corresponds to the carrier 1); and then a portion of the side chains (A') is converted to the non-reactive and hydrophilic side chains (B').

According to the process (1), first, polydichlorophosphazene is produced according to a conventional process, and the polydichlorophosphazene is reacted with (i) an organic compound which can be converted to the side chain (A') having functional group(s) capable of immobilizing a biologically active substance or group(s) which can be converted by a further treatment to group(s) capable of immobilizing a biologically active compound and with (ii) an organic compound which can be converted to the non-reactive and hydrophilic side chains (B'), at a desired ratio and in a desired order. The reaction conditions for this reaction are not critical, and can be determined according to the nature of the side chains to be introduced. Note, where the introduced group is a precursor for the reactive functional group, the former can be converted to a functional group which can be reacted with a biologically active substance by a conventional procedure.

According to the process (2), after polydichlorophosphazene is produced as described above, the polydichlorophosphazene is reacted with a primary alcohol or a phenol, such as trifluoroethanol, to prepare a polydialkoxyphosphzene which can be easily shaped, and the latter is shaped to form a film, fiber, rod or the like. Next, polyphosphazene side chains present at least in a surface layer portion of the shaped article are converted to the above-mentioned side chains (A') and/or (B'), as described above. In this case, again, the reaction conditions are not critical and may be determined depending on the nature of the organic compounds used to introduce the side chains.

Note, this process can be carried out in a solution to obtain a 100% substitution. The term "100% substitution" means that side chains are introduced throughout the article rather than only into the surface layer portion. In this case, a product is obtained that is substantially the same as that obtained from the process (1). Their direct introduction into polydichlorophosphazene of certain side chains (A') and (B') is difficult, and in such case the solution method is most suitable.

According to the process (3), the functional group capable of immobilizing a biologically active substance, introduced in the process (1) or (2) is further reacted with a hydrophilic organic compound. Although the hydrophilic organic compound may be any compound which provides the above-mentioned hydrophilic side chain, a compound containing (i) a functional group which reacts with the functional group capable of immobilizing a biologically active substance as well as (ii) a hydroxyl group and/or an ethylenoxy unit is preferable. For example, if the functional group capable of immobilizing a biologically active substance is an aldehyde group, cyanogen bromide-activated hydroxyl group, cyanogen bromide-activated amino or diazotized aromatic amino group, then monoethanolamine, tris-hydroxymethylaminomethane, 2-aminoethoxyethanol or the like is preferably used, and monoethanolamine is most preferable.

Where the functional group is a carboxyl group, a dehydrating agent such as carbodiimide, is used or after conversion to an active ester, the carboxyl group is preferably reacted with ethanolamine, tris-hydroxymethylaminomethane, 2-aminoethoxyethanol or the like. In this case monoethanolamine is most preferably used.

To convert a portion of the side chains having the functional group capable of immobilizing a biologically active substance to hydrophilic side chains, the functional group may be reacted to form a hydroxyl group and/or an ethylenoxy unit. For example, where the functional group is an amino group, a portion of the amino groups can be preferably reacted with formaldehyde to form a hydroxymethyl or reacted with an epoxyde compound. Where the functional group is a carboxyl or aldehyde group, it is preferably reduced to an alcohol, using a reducing agent.

As defined in the above-mentioned processes, embodiments for introducing a functional group capable of immobilizing a biologically active substance into a polyphosphazene polymer are described as follows.

Where the functional group to be introduced is an amino group, polydichlorophosphazene is obtained according to a conventional procedure, and reacted with a corresponding alcohol or phenol, or a metal salt thereof to form polydialcoxyphosphazene or polyaryloxyphosphazene. In this case, an amino alcoxide or aryloxide having a group non-reactive with the polydichlorophosphazene and convertible to an amino group is selectively used to introduce an aminoalcoxyl or aminoaryloxy group so that a phosphazene polymer having desired side chains is obtained. The group non-reactive with the polyphosphazene and to be converted to an amino group is, for example, a nitro group.

Such side chains having an amino group are exemplified as follows:

—OCH$_2$CH$_2$NH$_2$

—OCH$_2$CHCH$_2$NH$_2$
    |
    OH

—OCH$_2$CH$_2$OCH$_2$CH$_2$NH$_2$

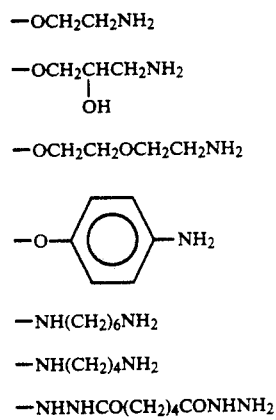

—NH(CH$_2$)$_6$NH$_2$

—NH(CH$_2$)$_4$NH$_2$

—NHNHCO(CH$_2$)$_4$CONHNH$_2$

Where the amino group is diazotized and the diazotized amino group is used as a functional group for immobilizing a biologically active group, first an aromatic amino group is introduced and then the amino group is diazotized. Note, a cyanogen bromide-activated amino group may be used.

Where the functional group capable of immobilizing a bilogically active substance is an aldehyde group, after preparing a phosphazene polymer which has side chains having an amino group, the phosphazene polymer is treated with a large excess amount of a dialdehyde, such as glutalaldehyde, to react with the amino group with only one aldehyde group of the dialdehyde compound. Alternatively, polydichlorophosphazene or polydialcoxyphosphazene is reacted with an alcohol or phenol having an aldehyde group which has been protected with an acetal bond, followed by deprotecting the acetal.

Where the functional group is a carboxyl group, polydichlorophosphazene or polydialcoxyphosphazene prepared according to a conventional procedure is reacted with a dialkali metal salt of a hydroxycarboxylic acid so that the alcoxy group of the hydroxycarboxylic acid salt is selectively reacted with the polydichlorophosphazene or polydialcoxyphosphazene to obtain a phosphazene polymer which has side chains having a carboxyl group. The carboxyl group thus introduced may be converted to a active ester prior to reaction with a biologically active substance.

Where the functional group is a hydroxyl group, for example, polydichlorophosphazene or polydialcoxyphosphazene prepared according to a conventional procedure is reacted with a mono-alkali metal salt of a diol. Since it is usually difficult to react the hydroxyl group thus introduced with a biologically active substance, it is activated with cyanogen bromide prior to the immobilization of a biologically active substance.

Where the functional group is an epoxy group, polydichlorophosphazene is reacted with a compound having an epoxy and hydroxyl groups in the presence of a base, at a low temperature. Alternatively, after introducing a compound having a halohydrin group into side chains of the phosphazene polymer, the phosphazene polymer is treated with an alkali to introduce an epoxy group into the side chain.

Alternatively, a functional group other than a functional group reactive with a biologically active group is introduced into side chains of the phosphazene polymer, and then the phosphazene polymer is treated with a compound which has both (i) a functional group reactive with the former functional group and (ii) a functional group reactive with a biologically active substance (or a corresponding protected group or a precursor group of the corresponding functional group) and then, if necessary, the protected group is deprotected or the precursor group is converted to a corresponding functional group.

Among the above-mentioned processes, the most preferable process is that wherein a polyphosphazene which has side chains having an amino group is prepared, and the polyphosphazene is reacted with a difunctional aldehyde compound such as glutalaldehyde, so that one of the two aldehyde groups of the difunctional aldehyde compound is bonded to the amino group of the polyphosphazene side chains.

Next, among the above-mentioned processsses, as examples of preparing a phosphazene polymer which has side chains having an aldehyde group reactive with a biologically active substance, the processes for the production of phosphazene polymer which has non-reactive and hydrophilic side chains in addition to the side chain having the aldehyde functional group are described in detail.

According to the first process, a shaped polyphosphazene article at least a surface layer portion of which is composed of a phosphazene polymer that has side chains having a primary amino group is treated with a solution containing a difunctional aldehyde and formaldehyde so that a functional group capable of immobilizing a biologically active substance (note, the biologically active substance is sometimes designated "ligand"; and the functional group is sometimes designated "ligand immobilizing group") and an organic group which is hydrophilic and non-reactive with a ligand are simultaneously introduced. In this case, the number of the ligand immobilizing groups and the number of the non-reactive and hydrophilic side chains can be controlled at will by adjusting a ratio of the difunctional aldehyde to formaldehyde and a ratio of their reactivities. On the contrary, a process wherein a difunctional aldehyde and formaldehyde are separately reacted tends to lead a deficiency of the ligand immobilizing group and an unnecessary crosslinking by difunctional aldehyde, because it is difficult to control a ratio of ligand immobilizing groups and non-reactive hydrophilic side chains in a final product such as a carrier for immobilizing a biologically active substance.

In the above-mentioned process, the difunctional aldehyde is preferably, but not limited to, glutalaldehyde, due to its low cost and easy handling. The difunctional aldehyde and formaldehyde are usually dissolved in water or an organic solvent, and the polyphosphazene article is treated in this solution. The organic solvent is preferably that which swells at least a surface layer portion of the article, and for the phosphazene polymer, for example, an alcohol such as methanol or an ethanol, an ether such as diethyl ether, or a mixture thereof, can be used. Moreover, such a good solvent can be mixed with a poor solvent, and among them, methanol and ethanol are preferable, and methanol is most preferable.

Although the concentration of a difunctional aldehyde and formaldehyde in a solvent is not critical, a total concentration of a difunctional aldehyde and formaldehyde in a solution is preferably about 0.01 to 15%, more preferably about 0.02 to 3% by weight.

A ratio of a difunctional aldehyde and formaldehyde (the former/the latter) is 1/100,000 to 1/1, preferably 1/10,000 to ½, most preferably 1/1,000 to 1/5 by mole. If a ratio of a difunctional aldehyde is higher than the upper limit, crosslinking tends to occur; on the other hand, if the ratio is lower than the lower limit, the aldehyde groups necessary to immobilize a sufficient amount of a ligand cannot be introduced.

A ratio of such a solution containing aldehydes to a shaped article composed of phosphazene polymer having amino groups in at least in a surface layer portion thereof is not critical, and usually the former is 0.1 to 100 times by weight of the latter.

In the above-mentioned reaction, since a difunctional aldehyde and formaldehyde are simultaneously reacted with the polyphosphazene article, the reaction proceeds competitively. Therefore, depending on the reactivity of both the reactants, both end aldehyde groups of the difunctional aldehyde compound may react, resulting in a crosslinking. Therefore, to prevent the crosslinking, preferably an organic acid such as formic acid, acetic acid, propionic acid or phenol, especially acetic acid, is added to the aldehyde solution.

A pH value of the adlehyde solution varies depending on a particular solvent used, and is usually 1.5 to 12, preferably 1.5 to 10. If the pH value is too low, the reaction of the aldehyde group with a primary amine is inhibited, and moreover, a crosslinking of the primary amino group by formaldehyde tends to occur. Therefore, a too low pH value is not preferable. On the other hand, if the pH value is too high, the reaction of aldehyde group with a primary amine is again inhibited, and where the aldehyde compound has an α-hydrogen, a side reaction such as aldol condensation may occur, and thus a too high pH value is not preferable.

Reaction conditions using the aldehyde solution may vary depending on the nature of a difunctional aldehyde used and, aldehyde concentration of the solution and the like, and usually the reaction is carried out at a room temperature until the primary amino group disappears. This time is usually about 10 minutes.

Since an imino bond formed by the reaction of the primary amino group and the aldehyde group is easily hydrolized, the imino bond is usually reduced to stabilize same. The preferable reducing agent is borane-dimethylamine complex, borane-trimethylamine complex, sodium cyanoborohydride or the like.

According to the second process, a shaped article composed of phosphazene polymer which has side chains having a primary amino group is reacted with a difunctional aldehyde compound to introduce ligand immobilizing groups, and then the remaining primary amino groups are diazotized, followed by hydrolysis to form hydroxyl groups. In this case, as a reaction medium for a reaction of the difunctional aldehyde, an aqueous solution adjusted to a pH of 1.5 to 5, preferably 1.7 to 3.5, is used. If a pH value at which the difunctional aldehyde compound is reacted with the primary amino group is lower than 1.5, then the reactivity of both reactants is very low, and a desired amount of ligand immobilizing groups cannot be introduced. On the other hand, if the pH value is higher than 5, the reactivity of the primary amine group with the aldehyde group is too high, and thus that both the aldehyde groups of the difunctional aldehyde compound react, resulting in crosslinking.

The pH value of the aldehyde solution may be adjusted with an aqueous solution of an acid, such as an inorganic acid such as hydrochloric acid, sulfuric acid, phosphoric acid or the like, or an organic acid such as acetic acid. Hydrochloric acid and sulfuric acid is preferable. Alternatively a mixture of an inorganic acid and an organic acid can be used.

In the above-mentioned process, the difunctional aldehyde compound is preferablely water soluble, and is especially glutalaldehyde. Although the concentration of difunctional aldehyde in solution is not critical, too high a concentration tends to lead to crosslinking, and too low a concentration does not introduce a sufficient amount of the ligand immobilizing group. Therefore, the concentration is usually about 0.01 to 15%, preferably 0.02 to 3%, by weight. The ratio of the difunctional aldehyde and the shaped article composed of phosphazene polymer which has side chains having a primary amino group is not critical, and usually a ratio of the difunctional aldehyde to the shaped article is 0.1 to 100 by weight.

In this process, next the remaining primary amino groups are diazotized, and the resulting diazonium salt is hydrolyzed to form hydroxyl groups. Since the reaction is carried out under a strongly acidic condition, the imine bond formed by a reaction of the aldehyde compound tends to be hydrolyzed. Therefore, to prevent the hydrolysis, the imine bond is preferably reduced prior to the diazotizing reaction. As the reducing agent, borane-dimethylamine complex, sodium cyanoborohydride, borane-trimethylamine complex, or tetramethylammonium boro hydride is preferably used. If the reduction is not carried out, the finally obtained carrier, when used in an affinity chrommatography, sometimes causes a non-specific adsorption, resulting in low separation efficiency, although the reason for this is not clear.

In the reduction of the imino bond, if an attempt is made to carry out the reaction to completion, an aldehyde group intended to be used for immobilizing a ligand is reduced even if a reducing agent is carefully chosen, and a pH of the reaction becomes 5, resulting in a reaction of the aldehyde group with a primary amino group, and thus the aldehyde groups available for immobilizing a ligand are reduced. Therefore, prior to the reduction of the imine bond, the aldehyde groups are preferably blocked.

To block the aldehyde groups, any blocker may be used as long as it can be easily deprotected. The aldehyde group is preferably blocked by an acetal bond. As an alcohol used to form the acetal bond, an alcohol having up to three carbon atoms, such as methanol, ethanol, ethyleneglycol or the like, can be used. For the acetal formation, an acid catalyst is usually used. The acid catalyst is, for example but not limited to, sulfuric acid, paratoluene sulfonic acid or the like. Since the shaped article has been soaked in an acidic medium having a pH value of 1.5 to 5 prior to the acetal formation, a small amount of the acid catalyst is sufficient. Usually, 10 to 10,000 parts by weight of alcohol and 0.01 to 1 part by weight of acidic catalyst per 1 part by weight of polyphospazene polymer are used. The reaction temperature is chosen so that an acetal bond is formed at an atmospheric pressure and the shape of the shaped phosphazene polymer is maintained, and is preferably 60° C. to 120° C. If an alcohol used has a boiling point in this temperature range, the reaction can be carried out while refluxing the alcohol.

Next, in the article whose aldehyde groups, which are ligand immobilizing groups, have been protected as above, the imine bonds formed by a reaction of a primary amino group with an aldehyde group is completely reduced. The reducing agent is, for example, sodium borohydrid, borane, borane-dimethylamine complex, sodium cyanoborohydride, borane-trimethylamine complex, tetramethylammonium hydride, lithium alminium hydride or the like, and among them, sodiumborohidride and borane are most preferable. For the reaction medium, when a boron-containing reducing agent is used, a lower alcohol such as methanol or ethanol, or water is used, and when a aluminium-containing reducing agent is used, an etheric solvent such as tetrahydrofuran, diethyl ether, dioxane or the like is preferably used.

A ratio of an amount of phosphazene polymer, an amount of reducing agent, and an amount of a reaction medium varies depending on a reducing power of the reducing agent, the stability of the reducing agent, and the like, and is usually 0.005 to 10 parts by weight of a reducing agent and 2 to 1,000 parts by weight of a reaction medium per 1 part by weight of polyphosphazene polymer, are used. The reaction time and reaction temperature vary depending on the above-mentioned factors, and usually are for 5 minutes to 20 hours at a room temperature.

Thus, the shaped article to which ligand immobilizing groups have been introduced, and which contains primary amino groups and aldehyde groups, is washed with water preferably having the same pH value as that for the reaction of the difunctional aldehyde compound, or more preferably, with a buffer solution having the same pH, to be used for a further reaction. The shaped article wherein ligand immobilizing groups have been blocked and imine bond have been reduced is washed with water, or with an lower alcohol having 1 to 3 carbon atoms, such as ethanol, to be used for a further reaction.

Next, the shaped article thus prepared is usually soaked in an acid to protonate all at the remaining amino groups, and reacted with a sodium nitrite aqueous solution under the acidic condition to form a diazonium salt, followed by a reaction with water to introduce hydroxyl groups. In this case, an acid concentration is preferably rather high, to thus accelerate the protonation inside phosphazene polymer, and usually, 1 N chlorohydric acid is preferably used. An amount of an acid used herein depends on the acid concentration, and is at least one time, or preferably at least 20 times that of the shaped article.

The concentration of sodium nitrite is preferably rather high, to thus accelerate the penetration of the salt into the phosphazene polymer, and usually, 0.1 to 2 M, preferably 0.3 to 1.5 M, of sodium nitrile is used.

The amount of sodium nitrite used must more than that of the primary amino groups present in whole phosphazene polymer, by mole. Since there is a possibility that nitrous acid generated during the diazotizing reaction escape without participating in reaction, and sometimes an amount of remaining primary amino group after a preceding crosslinking reaction and introduction of ligand immobilizing groups will not be clear, sodium nitrite is used preferably in an amount of at least 110% by mole of the primary amino groups present in the phosphazene polymer. The use of sodium nitrite in an amount less than that defined above would leave the primary amino groups unreacted, resulting in a non-specific adsorption when a corresponding final product is used.

Since the reaction for converting the primary amino group to a hydroxyl group proceeds very easily at a room temperature, when the generation of nitrogen gas stops, the reaction has been almost completed; it is possible to accelerate the completion of the reaction by a subsequent alkaline treatment or heating.

Since the conversion of the primary amino group to a hydroxyl group proceeds via carbonium ion, the reaction is frequently accompanied by a rearrangement. Although the rearrangement occurs so that more stable carbonium ions are formed, since the reaction is very complicated it is difficult to identify the reaction products. In many cases, however, even though the rearrangement occurs, since the hydroxy groups are introduced, no problem arises if resulting side chain is hydrophilic and crosslinking does not occur. Note, where the side chain contains the following structure, the rearrangement can be prevented;

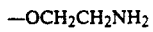

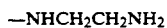

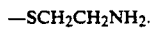

Next, in the shaped article wherein the primary amino groups have been converted to hydroxyl groups, the protected aldehyde groups are deprotected. The deprotection method varies depending on the protecting group. Namely, where an aldehyde group has been protected by formation of an acetal bond, the deprotection can be carried out by hydrolysis using an acid catalyst. The acid catalyst is preferably, but is not limited to, hydrochloric acid, sulfuric acid or paratoluenesulphonic acid, which is usually used as a 0.01 N to 2 N aqueous solution. A ratio of the acid aqueous solution and the shaped article is not critical, and usually, 5 to 1,000 parts by weight of the acid aqueous solution per 1 part by weight of the shaped article is used. A solvent miscible with water, such as an alcohol, may be added to the acid aqueous solution. The reaction time is not limited as long as the acetal is hydrolyzed at an atmospheric pressure and the shape of the shaped polymer article is maintained, but is usually 60° C. to 120° C.

If the phosphazene polymer thus obtained is water soluble or very sticky, it is prefer to crosslink a portion of side chains of the phosphazene polymer. The crosslinking can be carried out between functional groups capable of immobilizing a biologically active substance (ligand immobilizing groups) using an appropriate difunctional reagent reactive with the above-mentioned functional groups. Alternatively, functional groups which can crosslink under a particular condition are previously introduced to a phosphazene polymer, and then the introduced functional groups react under the particular condition to form crosslinkages. In another embodiment, first phosphazene polymer crosslinked with a difunctional reagent is prepared, and then the ligand immobilizing groups and the hydrophilic groups are introduced to the crosslinked phosphazene polymer.

Among the above-mentioned processes, where the phosphazene polymer has side chains having a primary amino group, this amino group is preferably used to form crosslinkages. A functional group capable of reacting with the primary amino group for the crosslinking is, for example, an aldehyde group, carboxyl group, ester group, epoxy group, acid anhydride or the like, and among them, the aldehyde group and epoxy group are preferable because they react at a room temperature. As an organic compound containing such functional groups, glutalaldehyde containing two aldehyde groups is preferable.

An organic compound containing at least two functional groups reactive with an amino group is used in a crosslinking reaction in the form of a 0.001% to 5%, preferably 0.01% to 3%, solution. If the concentration of the organic compound is lower than the above-defined lower limit, the amino groups are not sufficiently crosslinked, and the handling properties in subsequent steps become poor. On the other hand, since a high concentration of the di- or polyfunctional compound largely increases the crosslinking, when a finally produced carrier is used in, for example, an affinity chromatography, an adsorption/desorption rate of relevant substances to the carrier is lowered, resulting in a lowering of the concentration level of a desired substance. Note, in the crosslinking reaction, it is preferable to use a substance which can swell the phosphazene polymer, because a network of the crosslink is thereby expanded, resulting in a high adsorption/desorption rate of relevant substances to ligands in the carrier.

The crosslinking reaction is carried out after the shaping or during the shaping of a phosphazene polymer having primary amino acids on at least a portion of side chains thereof, or after the shaping of a phosphazene polymer having a high shapability and converting side chains present in at least a portion of a phosphazene polymer to side chains having a primary amino group using, for example, an amino alcoxide compound.

The article of the present invention may have any shape as far as it can immobilize biologically active substances, and is preferably, spherical, fibrous or film type. Spherical carrier preferably has an average diameter of 0.1 μm to 2 cm. Fibrous carrier preferably comprises filaments or staple fibers having an average diameter of 0.1 μm to 1,000 μm.

Since the present carrier exhibits very low nonspecific adsorption, when it is used in an affinity chromatography, it prevents contamination by impure proteins, and provide a desired product in a highly pure state. Moreover the present carrier is advantageous in that it has very high durability in contrast to conventional carriers made from carbohydrates, such as agarose or cellulose, which are easily contaminated with fungi. Moreover, since all side chains other than those which have a functional group immobilizing a biologically active substance are non-reactive and hydrophilic, then the decrease of reactivity between a biologically active substance on the carrier and a desired substance to be separated is very small, resulting in improved separation efficiency of the desired substance.

The biologically active substance-immobilized carrier of the present invention is also useful as an immobilized enzyme, a diagnostic agent and the like. In these uses, there are many advantages such as; less inactivation of the enzyme activity, improved sensitivity of the diagnostics, decreased possibility of incorrect result.

Since in the biologically active substance (ligand)-immobilized carrier, substantially all side chains other than the side chains on which a ligand has been immobilized are non-reactive and hydrophilic, it does not non-specifically adsorb proteins, and immobilized ligand does not encounter the change of its steric configuration and therefore does not lose its activity. Therefore, where the present carrier is used in an affinity chromatography, a desired product can be highly efficiently obtained in a highly purified form.

EXAMPLES

The present invention will now be further illustrated by, but is by no means limited to, the following examples.

EXAMPLE 1

Sodium alcoxide was prepared from 105 g of 2-(2-aminoethoxy)ethanol and 2.0 g of metallic sodium.

To this solution, 1.2 g of polybis(trifluoroethoxy) phosphazene fiber (single filament 20 de, 5 filaments) was soaked at 80° C. for 15 minutes to substitute 71% of side chains with 2-(2-aminoethoxy) ethoxy group as determined by measuring trifluoroethanol derived from the trifluoroethoxy group using a gas chromatography. Moreover, it was confirmed that substantially all side chains present in a surface layer portion of the polyphosphazene fiber were substituted by primary amino groups, by the facts that in an infrared spectrum method (ATR method) a wide peak at 3,500 to 3,300 cm$^{-1}$ designated to amino group was found, and that an absorbance designated to trichloroethoxy group disappeared. Note, the thickness of the surface layer portion means the depth of light penetrating into the fiber determined by ATR method at angle of incidence of 45° using a KRS-5 prism.

The polyphosphazene fiber thus obtained was six times washed with 500 ml of water for one hour, and soaked in 200 ml of 25% glutaraldehyde aqueous solution (adjusted to pH 6.5) at a room temperature for 3 hours. The fiber was washed with water and then three times with 100 ml of methanol.

The fiber was soaked in 100 ml of 90 mM monoethanolamine in 0.1 M phosphate buffer (pH 7.6) for three hours to convert 90% of all aldehyde groups to non-reactive and hydrophilic organic radicals. The fiber was washed with water, and three times with 100 ml of 0.1 M phosphate buffer (pH 7.6). After draining the solution, the fiber was soaked in 100 ml of a solution containing 30 mg of trypsin inhibitor in 0.1 M phosphate buffer (pH 7.6). An amount of trypsin inhibitor immobilized by the phosphazene polymer fiber was 27.2 mg as determined by measuring absorbance at 280 nm before and after the soaking. To the phosphazene polymer fiber was added 50 mg of sodium cyanoborohydride, incubated at 0° C. for 2 hours, and washed three times with 100 ml of 0.1 M phosphate buffer (pH 7.6).

The polyphosphazene fiber which immobilized 27.2 mg of trypsin inhibitor was soaked in 100 ml of 0.1 M phosphate buffer (pH 7.6) containing 30 mg of trypsin at 0° C. for one hour, and washed with 50 ml of 0.1 M phosphate buffer (pH 7.6) three times each for one minute.

Next, the fiber was soaked in 0.1 N hydrochloric acid aqueous solution at 0° C. to elute the adsorbed trypsin. An amount of the eluted trypsin was 19.6 mg as determined by measuring the absorbance at 280 nm of the elute after neutralizing it.

Next the polyphosphazene fiber was washed alternatively with 0.1 M phosphate buffer (pH 7.6) and 0.1 N hydrochloric acid aqueous solution each two times, and the above-mentioned adsorption/elution treatment was repeated, and in each case an amount of eluted trypsin was measured.

| Run No. | 1 | 2 | 3 | 4 | 5 | 6 | 7 | 8 |
|---|---|---|---|---|---|---|---|---|
| Eluted trypsin (mg) | 19.6 | 19.5 | 19.6 | 19.4 | 19.7 | 19.5 | 19.4 | 19.6 |

COMPARATIVE EXAMPLE 1

According to the procedure described in Example 1, convertion of side chains present in a surface layer portion of phosphazene polymer to 2-(2-aminoethoxy) ethoxy group, treatment with glutaraldehyde, washing with water, soaking in water, washing with 0.1 M phosphate buffer, draining of the solution, and soaking in 100 ml of 0.1 M phosphate buffer (pH 7.6) containing 30 mg of trypsin inhibitor at 0° C. for three hours were repeated. As a result, 27.3 mg of the trypsin inhibitor was immobilized. To the fiber, was added 50 mg of sodium cyanoborohydride, and incubation was carried out at 0° C. for two hours. After washing, an amount of eluted trypsin was determined as described in Example 1. As seen from the following result, since the aldehyde groups which have not reacted with trypsin inhibitor were not converted to non-reactive and hydrophilic groups, the activity of trypsin inhibitor was decreased.

| Run No. | 1 | 2 | 3 | 4 | 5 | 6 | 7 | 8 |
|---|---|---|---|---|---|---|---|---|
| Eluted trypsin (mg) | 11.5 | 10.9 | 11.3 | 11.4 | 10.9 | 11.3 | 11.2 | 11.5 |

EXAMPLE 2

The procedure described in Example 1 was carried out until the steps of soaking in glutaraldehyde, washing with water and washing with methanol, and the resulting polyphosphazene fiber was soaked in 100 ml of 0.1 M phosphate buffer (pH 7.6) containing 90 mM concentration of an organic compound shown in the following Table, to inactivate 90% of total aldehyde groups.

The fiber was treated as described in Example 1 to immobilize 25 mg of trypsin inhibitor. Next, sodium cyanoborohydride was similarly added after incubation and the fiber was washed. This polyphosphazene fiber which has immobilized 25 mg of trypsin inhibitor was soaked in 100 ml of rabbit serum in which 30 mg of trypsin has been dissolved at 0° C. for one hour, and three times washed with 50 ml of 0.1 M phosphate buffer (pH 7.6) at 0° C. each for one minute.

Next, the fiber was soaked in 0.1 N hydrochloric acid aqueous solution at 0° C. to elute adsorbed proteins.

After neutralization, the absorbance at 280 nm of the elute was measured to determine an amount of total protein using a calibration curve for trypsin. On the other hand, an amount of trypsin was determined by measuring enzyme activity in the elute. Where the difference between the amount of total protein determined by the absorbance and the amount of trypsin determined by enzyme activity was less than 1/100 on the basis of the amount of the trypsin, determined by the enzyme activity the result was considered as negative non-specific adsorption. Otherwise non-specific adsorption positive.

| Organic compound used | Non-specific adsorption |
| --- | --- |
| $NH_2CH_2CH_2OH$ | Negative |
| $NH_2CH_2CH_2CH_2OH$ | Negative |
| $NH_2CH_2CH_2OCH_2CH_2OH$ | Negative |
| $NH_2-\underset{\underset{CH_2OH}{\|}}{\overset{\overset{CH_2OH}{\|}}{C}}-CH_2OH$ | Negative |
| $NH_2CH_2CH_2CH_2CH_3$ | Positive* |
| $NH_2CH_2CH_2OCH_3$ | Negative |
| $NH_2CH_2CH_2OCH_2CH_2OCH_3$ | Negative |
| $NH_2(CH_2CH_2O)_3C_4H_9$ | Negative |
| $NH_2(CH_2CH_2O)_3C_5H_{12}$ | Positive* |
| $NH_2(CH_2CH_2O)_3C(CH_3)_2CH_2OH$ | Negative |
| $NH_2(CH_2CH_2O)_4OH$ | Negative |
| $NH_2CH_2\underset{\underset{OH}{\|}}{C}HCH_2CH_2OH$ | Negative |
| $NH_2CH_2\underset{\underset{OH}{\|}}{C}HCH_2CH_2CH_2CH_2CH_2OH$ | Positive* |

*Comparative Examples.

EXAMPLE 3

According to the same procedure as described in Example 1, side chains present in a surface portion of a polyphosphazene fiber was converted to 2-(2-aminoethoxy) ethoxy group, the fiber was treated with glutaraldehyde, washed with water, soaked in methanol, washed with 20 mM acetate buffer (pH 4.9), and draining the solution, soaked in 100 ml of 20 mM acetate buffer (pH 4.9) containing 30 mg of invertase at 0° C. for 3 hours to immobilize 28.1 mg of invertase. The amount of immobilized invertase was determined from an amount of decreased invertase activity in a supernatant.

The fiber was washed with 20 mM acetate buffer solution (pH 4.9) and soaked in 400 ml of 1 M mono ethanolamine in 0.1 M phosphate buffer (pH 7.0) at 0° C. for 3 hours, to which 70 mg of sodium cyanoborohydride was then added. The whole was incubated at 0° C. for 2 hours.

The fiber was washed with 20 mM acetate buffer (pH 4.9), and the immobilized invertase activity was measured using 0.1 M sucrose solution as a substrate. The activity was 70 U/mg.

COMPARATIVE EXAMPLE 2

The same procedure as described in Example 3 was repeated except that the step of soaking in monoethanolamine solution was omitted. The enzyme activity remarkably decreased, and was 22 U/mg.

EXAMPLE 4

Polybis2-(2-aminoethoxy)phosphazene fiber prepared according to the same procedure as described in Example 1 was soaked in 200 ml of a mixture of the formaldehyde aqueous solution (30%)/glutaraldehyde aqueous solution (25%)/water in a volume ratio of 10/90/1, at a room temperature for 12 hours.

Next, the fiber was washed six times with 500 ml of water, three times with 100 ml of methanol and three times with 100 ml of 0.1 M phosphate buffer (pH 7.6). The fiber was soaked in 10 ml of 0.1 M phosphate buffer (pH 7.6) containing 5 mg of protein A at 0° C. for three hours to immobilize 4.8 mg of protein A.

The fiber was subjected to the reduction with sodium cyanoborohydride, washing with 0.1 M phosphate buffer (pH 7.6), soaking in 90 mM monoethanolamine in 0.1 M phosphate buffer, reduction with sodium cyanoborohydride, and washing with 0.1 M phosphate buffer (pH 7.6). Next, using 20 ml of 0.1 M phosphate buffer (pH 7.6) containing 20 mg of IgG, adsorption, washing, elution, and restoration of the fiber were carried out as described in Example 1. An amount of IgG adsorbed by protein A was 18.4 mg.

EXAMPLE 5

Polybis2-(2-aminoethoxy)phosphazene fiber prepared according to the same procedure as described in Example 1 was soaked in 200 ml of a mixture of formaldehyde aqueous solution (30%)/glutaraldehyde aqueous solution (25%)/water in a volume ratio of 10/90/1, at a room temperature for 12 hours.

The carrier fiber thus prepared was soaked in 20 ml of 20 mM phosphate buffer (pH 7.6) containing 20 mg of bovine serum albumin (BSA) for one hour, and an amount of bovine serum albumin immobilized on the fiber was determined by the decrease of the absorbance at 280 nm of supernatant as 18.5 mg.

The fiber was soaked in 100 ml of 90 mM monoethanolamine in 0.1 M phosphate buffer (pH 7.6) for 3 hours to block the remaining aldehyde groups, and resulting imine bonds were reduced with sodium cyanoborohydride. Next, 50 ml of rabbit serum obtained by immunization with BSA was applied to the carrier fiber, and affinity chromatographic procedure including adsorption, washing, elution and restoration of the carrier was carried out. An amount of eluted anti BSA antibody was 34.7 mg, and exhibited a single band in electrophoresis.

EXAMPLE 6

Sodium alcoxide was prepared from 105 g of 2-(2-aminoethoxy)ethanol and 2.0 g of metallic sodium.

To this solution, 1.2 g of polybis(trifluoroethoxy)-phosphazene fiber (single filament 20 de, 5 filaments) was soaked at 80° C. for 15 minutes to substitute 76% of side chains with 2-(2-aminoethoxy)ethoxy group as determined by measuring trifluoroethanol derived from the trifluoroethoxy group using a gas chromatography.

Note, an observation of the fiber by an optical microscope showed that the substitution reaction reached to the depth of about ⅔ from the surface of the fiber, but a boundary was not clear. Moreover, an infrared spectrum showed an absorption assigned to a primary amino group, revealing that a primary amino group was introduced to a side chain of the phosphazene polymer.

0.3 g of the fiber was soaked in 200 ml of a mixture of formaldehyde aqueous solution (30%)/glutaraldehyde aqueous solution (25%/10% acetic acid in methanol in a ratio of 10/1/90 at a room temperature for 12 hours.

Next, the fiber was washed 6 times with 50 ml of water, three times with 100 ml of methanol and three times with 100 ml of 0.1 M phosphate buffer (pH 7.6). The fiber was soaked in 10 ml of 0.1 M phosphate buffer (pH 7.6) containing 25 mg of bovine serum albumin (BSA) at 0° C. for 3 hours to immobilize 24.1 mg of BSA. To this, was added 50 mg of sodium cyanoborohydride, and after incubation at 0° C. for 2 hours, the polyphosphazene fiber was washed three times with 100 ml of 0.1 M phosphate buffer (pH 7.6).

The fiber was soaked in 100 ml of 90 mM monoethanolamine in 0.1 M phosphate buffer (pH 7.6) for 3 hours to block the remaining aldehyde groups, and formed imine bonds were reduced with sodium cyanoborohydride.

50 ml of rabbit serum obtained by immunizing with BSA was applied to the above-prepared carrier, and a procedure of affinity chromatography including adsorption, washing, elution and restoration was carried. An amount of eluted anti-BSA antibody was 41.3 mg, and the antibody was electrophoretically homogeneous.

EXAMPLE 7

The procedure described in Example 4 was repeated except that trypsin inhibitor was used in place of protein A, and a carrier on which 25 mg of trypsin inhibitor has been immobilized was obtained. According to the same procedure as described in Example 4, treatments with sodium cyanoborohydride, ethanolamine, etc was carried out. The carrier was evaluated for non-specific adsorption of proteins, and the non-specific adsorption was not detected.

EXAMPLE 8

A polyphosphazene fiber to which primary amino groups have been introduced according to the same procedure as described in Example 6 was run in water at a low speed for about 10 minutes to eliminate remaining sodium alcoholate, and pulled out, and to the fiber was immediately dropwise added a solution of 0.05% glutaraldehyde in acetone/water (1/1). After 5 minutes, the fiber was run in air to partially crosslinked, and 0.3 g of the fiber was soaked in 200 ml of a mixture of formaldehyde aqueous solution (30%)/glutalaldehyde aqueous solution (25%)/10% acetic acid in methanol in a ratio of 10/1/90 by volume at a room temperature for 12 hours.

Next, the fiber was washed 6 times with 50 ml of water, three times with 100 ml of methanol and three times with 100 ml of 0.1 M phosphate buffer (pH 7.6). The fiber was soaked in 10 ml of 0.1 M phosphate buffer (pH 7.6) containing 25 mg of bovine serum albumin (BSA) at 0° C. for 3 hours to immobilize 24.1 mg of BSA. To this, was added 50 mg of sodium cyanoborohydride, and after incubation at 0° C. for 2 hours, the polyphosphazene fiber was washed three times with 100 ml of 0.1 M phosphate buffer (pH 7.6).

The fiber was soaked in 100 ml of 90 mM monoethanolamine in 0.1 M phosphate buffer (pH 7.6) for hours to block the remaining aldehyde groups, and formed imine bonds were reduced with sodium cyanoborohydride.

50 ml of rabbit serum obtained by immunizing with BSA was applied to the above-prepared carrier, and a procedure of affinity chromatography including adsorption, washing, elution and restoration was carried out. An amount of eluted IgG was 32.4 mg, and the antibody was electrophoretically homogeneous.

EXAMPLE 9

A polyphosphazene fiber to which primary amino groups have been introduced according to the same procedure as described in Example 6 was run at a low speed in water for about 10 minutes to eliminate remaining sodium alcoholate, and reeled in water. The fiber was taken out, and soaked in 100 ml of a mixture of glutaraldehyde (25% aqueous solution)/0.01 N chlorohydric acid aqueous solution (1/100 by volume) (pH 1.9) at 0° C. for one hour. The fiber was washed three times with 100 ml of water, soaked in 50 ml of 1 N hydrochrolic acid at 0° C. for 3 hours, and 25 ml of 0.5 M sodium nitrite was added thereon. After generation of nitrogen was finished, the whole was allowed to stand at a room temperature for 3 hours, the fiber was washed three times with 100 ml of water, three times with 100 ml of methanol and three times with 100 ml of 0.1 M phosphate buffer (pH 7.6).

The carrier fiber thus prepared was soaked in 20 ml of 20 mM phosphate buffer (pH 7.6) containing 20 mg of bovine serum albumin, resulting in immobilization of 18.7 mg of the bovine serum albumin after one hour as determined by decrease of the absorbance at 280 nm of a supernatant.

The fiber was soaked in 100 ml of 90 mM monoethanolamine in 0.1 M phosphate buffer (pH 7.6) for 3 hours to block the remaining aldehyde groups, and formed imine bonds were reduced with sodium cyanoborohydride.

50 ml of rabbit serum obtained by immunizing with BSA was applied to the above-prepared carrier, and a procedure of affinity chromatography including adsorption, washing, elution and restoration was carried. An amount of eluted anti-BSA antibody was 34.1 mg, and the antibody was electrophoretically homogeneous.

EXAMPLES 10 TO 12 AND COMPARATIVE EXAMPLE 3

The same procedure as described in Example 1 was repeated except that condition for reaction with glutaraldehyde was different. An amount of immobilized bovine serum albumin (BSA) for each Example was as follows.

It is clear that an amount of immobilized bovine serum albumin (BSA) changes depending on pH value of a reaction solution.

| No. | Solvent | pH of solution | Glutaraldehyde (25% aq)/ solv. | Amount of immobilized BSA (mg) |
|---|---|---|---|---|
| Con. Ex. 3 | 0.1 N HCL aq. | 1.0 | 1/100 | 0 |
| Ex. 10 | 0.03 N HCl aq. | 1.5 | 1/100 | 16.7 |
| Ex. 11 | 50 mM acetate buffer | 5.0 | 1/100 | 16.3 |
| Ex. 12 | 50 mM phosphate buffer | 6.0 | 1/100 | 6.4 |

EXAMPLE 13

A polyphosphazene fiber to which primary amino groups have been introduced according to the same procedure as described in Example 6 was run in water at a low speed for about 10 minutes to eliminate remaining sodium alcoholate, and pulled out, and to the fiber was immediately dropwise added a solution of 0.05% glutaraldehyde in aceton/water (1/1). After 5 minutes, the fiber was run in air, and reeled in 100 ml of a mixture (pH 1.90) of glutaraldehyde (25% aqueous solution)/0.01 N hydrochrolic acid (1/100 by volume). The reeled fiber was released, and again soaked in the same mixture at a room temperature for one hour, and 50 mg of borane-dimethylamine complex boron was added thereon. After allowing to stand overnight at a room temperature, the fiber was washed with water and soaked in 50 ml of 1 N hydrochloric acid at 0° C. for 3 hours, and 25 ml of 0.5 M sodium nitrite aqueous solution was gradually dropwise added thereon. After generation of nitrogen was finished, the whole was allowed to stand at a room temperature for 3 hours, and the fiber was washed three times with 100 ml of water, three times 100 ml of methanol and three times with 100 ml of 0.1 M phosphate buffer (pH 7.6).

The carrier fiber thus obtained was soaked in 20 ml of 20 mM phosphate buffer (pH 7.6) containing 20 mg of bovine serum albumin for one hour, and an amount of the bovine serum albumin immobilized on the fiber was 18.5 mg as determined by decrease of the absorbance at 280 nm of a supernatant.

EXAMPLE 14

By soaking the carrier fiber prepared in Example 13 in 10 ml of 20 mM phosphate buffer (pH 7.6) containing 5 mg of protein A, 4.6 mg of protein A could be immobilized. To this was added 10 ml of 20 mM phosphate buffer containing 40 mg of borane dimethylamine complex, and the whole was allowed to stand at 0° C. for 2 hours and at a room temperature for 2 hours. The fiber was roughly washed with water, soaked in 0.4 M ethanolamine 0.1 M phosphate buffer (pH 7.1) at a room temperature for 5 hours, and 40 mg of borane dimethylamine complex was added thereon. After allowing to stand at a room temperature for 3 hours, the fiber was washed with 20 mM phosphate buffer (pH 7.6).

After thoroughly draining the solution, the fiber was soaked in 20 ml of 20 mM phosphate buffer (pH 7.6) containing 20 mg of human IgG, and washed with 20 mM phosphate buffer (pH 7.6). After thoroughly draining the buffer, the filter was soaked in 20 ml of 0.1 N hydrochrolic acid for 5 minutes to elute the human IgG. An amount of eluted human IgG was 17.5 mg as determined after neutralization. The fiber was washed with the same buffer, washed with 0.1 N hydrochrolic acid, and restored with the same buffer. The restored fiber was again soaked in human IgG solution, and subsequent steps were carried out. This procedure was repeated 10 times, and an amount of eluted human IgG in each run was shown in the following Table.

| Repeat No. | 1 | 2 | 3 | 4 | 5 | 6 | 7 | 8 | 9 | 10 |
|---|---|---|---|---|---|---|---|---|---|---|
| Eluted human IgG (mg) | 17.5 | 17.1 | 17.6 | 17.4 | 17.6 | 17.0 | 17.2 | 17.5 | 17.4 | 17.7 |

EXAMPLE 15

The fiber on which bovine serum albumin has been immobilized, described in Example 13, was subjected to the reduction, monoethanolamine-coupling reaction, etc., described in Example 14. Next, the fiber thus prepared was soaked in 40 ml of a rabbit serum obtained by immunizing with bovine serum albumin, washed and eluted as described in Example 14 to obtain 27.4 mg of anti-bovine serum albumin antibody, which was electrophoretically homogeneous.

EXAMPLES 16 TO 18 AND COMPARATIVE EXAMPLE 4

According to the same procedure as described in Example 13, primary amino groups were introduced in side chains of polyphosphazene, and the surface-treated fiber was run in water for about 10 minutes to eliminate remaining sodium alcoholate, and pulled out from water. To the fiber was dropwise added a solution of 0.05% glutaraldehyde in acetone/water (1/1). After that, the fiber was run in air for 5 minutes and soaked in the following glutaraldehyde solution, followed by treatment as described in Example 13. A result is shown in the following Table.

| No. | Solvent | pH of solution | Glutaraldehyde (25% aq)/solv. | Immobilized amount (mg) |
|---|---|---|---|---|
| Con. Ex. 4 | 0.1 N HCl aq. | 1.0 | 1/100 | 0 |
| Ex. 16 | 0.03 N HCl aq. | 1.5 | 1/100 | 16.7 |
| Ex. 17 | 50 mM acetate buffer | 5.0 | 1/100 | 16.3 |
| Ex. 18 | 20 mM phosphate buffer | 6.0 | 1/100 | 6.4 |

As seen from the above, the performance of the fibers in Examples 16, 17 and 18 as well as Comparative Example 4 is same as those of corresponding Examples 10, 11 and 12 as well as Comparative Example 3 respectively, and only handleability was improved.

EXAMPLE 19

A polyphosphazene fiber to which primary amino groups have been introduced according to the same procedure as described in Example 6 was run in water at a low speed, for about 10 minutes to eliminate remaining sodium alcoholate, and pulled out, and to the fiber was immediately dropwise added a solution of 0.05% glutalaldehyde in acetone/water (1/1). After that the fiber was run in air for 5 minutes, and reeled in 100 ml of a mixture (pH 1.90) of glutaraldehyde (25% aqueous solution)/0.01 N hydrochrolic acid (1/100 by volume). The reeled fiber was released, and again soaked in the same mixture at a room temperature for 15 hours.

The fiber was taken from the mixture, and after wiping off the mixture, soaked in 100 ml of ethanol containing 1 g of sodium borohydride at a room temperature for one hour. The fiber was washed with water, soaked in 50 ml of 1 N hydrochloric acid at 0° C. for one hour, and 25 ml of 0.5 M sodium nitrite was gradually dropwise added thereon at 0° C. After finishing generation of nitrogen, the reaction mixture was allowed to stand at a room temperature for 15 hours, and the filter was washed with water and soaked in a mixture of 50 ml 1 N hydrochrolic acid and 50 ml ethanol, and heated at 80° C. for one hour.

Next, the fiber was washed with water and 0.1 M phosphate buffer (pH 7.6).

The carrier fiber thus obtained was soaked in 100 ml of 0.1 M phosphate buffer (pH 7.6) containing 30 mg of soybean trypsin inhibitor at 0° C. for 3 hours to immobilize 27.2 mg of soybean trypsin inhibitor.

To the solution was added 50 mg of sodium cyanoborohydride, and the whole was allowed to stand at 0° C. for 2 hours. The polyphosphazene fiber was washed three times with 100 ml of 0.1 M phosphate buffer. Next, the fiber was soaked in 100 ml of 0.1 M phosphate buffer (pH 7.6) containing 90 mM monoethanolamine, and 50 mg of sodium cyanoborohydride was added thereon. The reaction mixture was allowed to stand for 2 hours, and the polyphosphazene fiber was washed with 0.1 M phosphate buffer (pH 7.6).

The fiber was soaked in 100 ml of rabbit serum containing 30 mg of soybean trypsin at 0° C. for one hour, and washed three times with 50 ml of 0.1 M phosphate buffer (pH 7.6) for one minute.

Next, the fiber was soaked in 0.1 N hydrochrolic acid at 0° C. for 10 minutes to elute the soybean trypsin previously adsorbed. After neutralizing the solution, an amount of the eluted soybean trypsin was 19.6 mg as determined by measuring an absorbance at 280 nm. The eluted soybean trypsin was electrophoretically homogeneous.

EXAMPLE 20

In accordance with the same procedure as described above, the fiber reeled in 100 ml of a mixture of glutalaldehyde (25% aqueous solution) and 0.01 N hydrochrolic acid (1:100 by volume) (pH 1.90) was released(?) and again soaked in the same mixture at a room temperature for 15 hours, and 250 mg of sodium cyanoborohydride was added thereon. The reaction mixture was allowed to stand at a room temperature for 10 hours. At this time, a pH value of the mixture was 9.8. The fiber was washed with 0.1 M phosphate buffer, soaked in hydrochloric acid as described in Example 19, diazotized with sodium nitrite, and washed. Next, soybean trypsin inhibitor was immobilized, and an amount of immobilized soybean trypsin inhibitor was 7.1 mg.

EXAMPLE 21

The carrier fiber obtained according to the same procedure as described in Example 19 was soaked in 20 ml of 0.1 M phosphate buffer (pH 7.6) containing 5 mg of protein A at 0° C. for three hours. As a result all 5 mg of the protein A was immobilized.

To the reaction mixture was added 30 mg of sodium cyanoborohydride, and the whole was allowed to stand at 0° C. for 2 hours. The polyphosphazene fiber was washed three times with 0.1 M phosphate buffer (pH 7.6). The fiber was soaked in 100 ml of 90 mM monoethanolamine in 0.1 M phosphate buffer (pH 7.6) for 3 hours, 30 mg of sodium cyanogen borohydride was added therein, and the whole was allowed to stand for 2 hours. The polyphosphazene fiber was washed with 0.1 M phosphate buffer (pH 7.6).

The fiber was soaked in 50 ml of 0.1 M phosphate buffer (pH 7.6) containing 50 mg of rabbit IgG and 20 mg of bovine serum albumin at 0° C. for one hour, and washed three times with 50 ml of 0.1 M phosphate buffer (pH 7.6) at 0° C.

Next, the fiber was soaked in 0.1 N hydrochloric acid at 0° C. for 10 minutes to elute the adsorbed rabbit IgG. The elute was neutralized, and an amount of eluted rabbit IgG was 43.9 mg as determined by measuring an absorbance at 280 nm of the elute. The eluted IgG was electrophoretically homogeneous.

We claim:

1. A carrier for immobilizing a biologically active substance, said carrier comprising ak phosphazene polymer having side chains, wherein the side chains of the phosphazene polymer present in at least a surface layer portion of the carrier consist essentially of (i) organic radicals having a functional group capable of binding the biologically active substance and (ii) organic radicals which are non-reactive and hydrophilic, wherein the non-reactive and hydrophilic organic radical is an organic radical formed by reacting a side chain of a phosphazene polymer having a primary amino group with formaldehyde.

2. A carrier for immobilizing a biologically active substance, said carrier comprising ak phosphazene polymer having side chains, wherein the side chains of the phosphazene polymer present in at least a surface layer portion of the carrier consist essentially of (i) organic radicals having a functional group capable of binding the biologically active substance and (ii) organic radicals which are non-reactive and hydrophilic, wherein the non-reactive and hydrophilic organic radical is an organic radical formed by diazotizing a side chain of a phosphazene polymer having a primary amino group, followed by hydrolysis to form a hydroxyl group.

3. The carrier of claim 1 or 2 wherein the carrier contains immobilized thereon a biologically active substance selected from the group consisting of enzyme, antibody, nucleic acid, co-enzyme and hapten.

4. A process for the production of a carrier for immobilizing a biologically active substance comprising the steps of:

(i) providing a shaped polyphosphazene article, wherein at least a surface portion of the article is composed of a phosphazene polymer which has side chains having primary amino groups; and (ii) reacting said primary amino groups of said side chains of the shaped polyphosphazene article with a solution containing a bifunctional aldehyde and formaldehyde, wherein a portion of said primary amino groups react with said bifunctional aldehyde to form side chains capable of binding a biologically active substance, and the remaining portion of said primary amino groups react with the formaldehyde to form side chains which are non-reactive and hydrophilic, so as to produce said carrier.

5. A process for the production of a carrier for immobilizing a biologically active substance comprising the steps of:

(i) providing a shaped polyphosphazene article, wherein at least a surface portion of the article is composed of a phosphazene polymer which has side chains having primary amino groups; and (ii) reacting a portion of the primary amino groups of said side chains of the shaped polyphosphazene article with a bifunctional aldehyde, wherein the reacting of said bifunctional aldehyde is at a pH value of between 1.5 and 5, to provide side chains capable of binding a biologically active substance, and then (iii) diazotizing primary amino groups remaining after step (ii), followed by hydrolysis to form hydroxyl groups to provide side chains which are non-reactive and hydrophilic, so as to produce said carrier.

6. A process for the production of a carrier for immobilizing a biologically active substance comprising the steps of:
(i) reacting a shaped polyphosphazene article with a bifunctional aldehyde, wherein at least a surface layer portion of the article is composed of a phosphazene polymer which has side chains having primary amino groups, and wherein the bifunctional aldehyde is reacted with a portion of the primary amino groups of the side chains, resulting in a reaction product containing aldehyde groups, so as to provide side chains capable of binding a biologically active substance;
(ii) blocking said aldehyde groups with a protecting agent, and reducing imino bonds formed by the treatment with the bifunctional aldehyde;
(iii) diazotizing primary amino groups remaining after step (ii), followed by hydrolysis to form hydroxy groups to provide side chains which are non-reactive and hydrophilic; and
(iv) removing the protecting groups, so as to produce said carrier.

7. A process for the production of a carrier for immobilizing a biologically active substance comprising the steps of:
(i) crosslinking a shaped polyphosphazene article, wherein at least a surface layer portion of the article is composed of phosphazene polymer which has side chains having primary amino groups;
(ii) reacting a portion of the primary amino groups of said side chains with a bifunctional aldehyde; and
(iii) converting primary amino groups of said side chains remaining after step (ii) to organic radicals which are non-reactive and hydrophilic, so as to produce said carrier.

* * * * *